(12) United States Patent
Soederstroem (10) Patent No.: US 9,081,488 B2
(45) Date of Patent: Jul. 14, 2015

(54) STIMULATION LEADWIRE AND VOLUME OF ACTIVATION CONTROL AND DISPLAY INTERFACE

(71) Applicant: BOSTON SCIENTIFIC NEUROMODULATION CORPORATION, Valencia, CA (US)

(72) Inventor: Anna Soederstroem, San Jose, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 275 days.

(21) Appl. No.: 13/651,942

(22) Filed: Oct. 15, 2012

(65) Prior Publication Data

US 2013/0104066 A1   Apr. 25, 2013

Related U.S. Application Data

(60) Provisional application No. 61/549,079, filed on Oct. 19, 2011.

(51) Int. Cl.
*G06F 3/0481* (2013.01)
*G06F 3/0484* (2013.01)
*A61B 5/00* (2006.01)
*G06F 19/00* (2011.01)
*A61N 1/372* (2006.01)
*A61N 1/05* (2006.01)
*A61N 1/36* (2006.01)

(52) U.S. Cl.
CPC .......... *G06F 3/04847* (2013.01); *A61B 5/4058* (2013.01); *A61B 5/7264* (2013.01); *A61N 1/37247* (2013.01); *G06F 19/3406* (2013.01); *G06F 19/3437* (2013.01); *G06F 19/3481* (2013.01); *A61B 5/4076* (2013.01); *A61N 1/0534* (2013.01); *A61N 1/3605* (2013.01)

(58) Field of Classification Search
USPC ........................................................ 715/771
See application file for complete search history.

(56) References Cited

U.S. PATENT DOCUMENTS 5,099,846 A   3/1992   Hardy
5,361,763 A   11/1994  Kao et al.
5,452,407 A   9/1995   Crook (Continued)

FOREIGN PATENT DOCUMENTS

WO   01/90876 A1   11/2001
WO   2004/019799 A2   3/2004

(Continued)

OTHER PUBLICATIONS

Butson et al., "Current Steering to Control the Volume of Tissue Activated During Deep Brain Stimulation," Brain Stimulation 1, 2008, pp. 7-15.

(Continued)

*Primary Examiner* — Matthew Ell
(74) *Attorney, Agent, or Firm* — Lowe Graham Jones PLLC; Bruce E. Black (57) ABSTRACT

A method and system include a processor that outputs a model of anatomical structures of a region in which a leadwire is implanted, the structures being distinguished by graphical indicia associated with respective textual descriptions in a legend. Electrodes of a model of the leadwire overlaid on the anatomical structure models are selectable, in response to which selection the processor displays a control for modifying an electrical setting of the selected contact.

19 Claims, 6 Drawing Sheets

(56) References Cited

U.S. PATENT DOCUMENTS

| | | | |
|---|---|---|---|
| 5,724,985 A | 3/1998 | Snell et al. | |
| 5,782,762 A | 7/1998 | Vining | |
| 5,938,688 A | 8/1999 | Schiff | |
| 6,066,163 A | 5/2000 | John | |
| 6,083,162 A | 7/2000 | Vining | |
| 6,106,460 A | 8/2000 | Panescu et al. | |
| 6,192,266 B1* | 2/2001 | Dupree et al. | 600/427 |
| 6,240,308 B1 | 5/2001 | Hardy et al. | |
| 6,289,239 B1 | 9/2001 | Panescu et al. | |
| 6,310,619 B1 | 10/2001 | Rice | |
| 6,319,241 B1 | 11/2001 | King et al. | |
| 6,351,675 B1 | 2/2002 | Tholen et al. | |
| 6,389,311 B1 | 5/2002 | Whayne et al. | |
| 6,463,328 B1 | 10/2002 | John | |
| 6,491,699 B1 | 12/2002 | Henderson et al. | |
| 6,539,263 B1 | 3/2003 | Schiff et al. | |
| 6,622,048 B1* | 9/2003 | Mann et al. | 607/46 |
| 6,690,972 B2 | 2/2004 | Conley et al. | |
| 6,694,162 B2 | 2/2004 | Hartlep | |
| 6,694,163 B1 | 2/2004 | Vining | |
| 6,748,098 B1 | 6/2004 | Rosenfeld | |
| 6,788,969 B2 | 9/2004 | Dupree et al. | |
| 6,795,737 B2 | 9/2004 | Gielen et al. | |
| 6,827,681 B2 | 12/2004 | Tanner et al. | |
| 6,830,544 B2 | 12/2004 | Tanner | |
| 6,909,913 B2 | 6/2005 | Vining | |
| 7,003,349 B1 | 2/2006 | Andersson et al. | |
| 7,003,352 B1 | 2/2006 | Whitehurst | |
| 7,008,370 B2 | 3/2006 | Tanner et al. | |
| 7,035,690 B2 | 4/2006 | Goetz | |
| 7,043,293 B1 | 5/2006 | Baura | |
| 7,050,857 B2 | 5/2006 | Samuelsson et al. | |
| 7,107,102 B2 | 9/2006 | Daignault, Jr. et al. | |
| 7,136,518 B2 | 11/2006 | Griffin et al. | |
| 7,136,695 B2 | 11/2006 | Pless et al. | |
| 7,146,219 B2 | 12/2006 | Sieracki et al. | |
| 7,146,223 B1 | 12/2006 | King | |
| 7,151,961 B1 | 12/2006 | Whitehurst et al. | |
| 7,155,279 B2 | 12/2006 | Whitehurst et al. | |
| 7,167,760 B2 | 1/2007 | Dawant et al. | |
| 7,177,674 B2 | 2/2007 | Echauz et al. | |
| 7,181,286 B2 | 2/2007 | Sieracki et al. | |
| 7,184,837 B2 | 2/2007 | Goetz | |
| 7,209,787 B2 | 4/2007 | DiLorenzo | |
| 7,216,000 B2 | 5/2007 | Sieracki et al. | |
| 7,217,276 B2 | 5/2007 | Henderson et al. | |
| 7,218,968 B2 | 5/2007 | Condie et al. | |
| 7,231,254 B2 | 6/2007 | DiLorenzo | |
| 7,239,910 B2 | 7/2007 | Tanner | |
| 7,239,926 B2 | 7/2007 | Goetz | |
| 7,242,984 B2 | 7/2007 | DiLorenzo | |
| 7,252,090 B2 | 8/2007 | Goetz | |
| 7,254,446 B1 | 8/2007 | Erickson et al. | |
| 7,257,447 B2 | 8/2007 | Cates et al. | |
| 7,266,412 B2 | 9/2007 | Stypulkowski | |
| 7,295,876 B1 | 11/2007 | Erickson | |
| 7,313,430 B2 | 12/2007 | Urquhart et al. | |
| 7,324,851 B1 | 1/2008 | DiLorenzo | |
| 7,346,382 B2 | 3/2008 | McIntyre et al. | |
| 7,388,974 B2 | 6/2008 | Yanagita | |
| 7,463,928 B2 | 12/2008 | Lee et al. | |
| 7,499,048 B2 | 3/2009 | Sieracki et al. | |
| 7,505,815 B2 | 3/2009 | Lee et al. | |
| 7,548,786 B2 | 6/2009 | Lee et al. | |
| 7,603,177 B2 | 10/2009 | Sieracki et al. | |
| 7,617,002 B2 | 11/2009 | Goetz | |
| 7,623,918 B2 | 11/2009 | Goetz | |
| 7,657,319 B2 | 2/2010 | Goetz et al. | |
| 7,676,273 B2 | 3/2010 | Goetz et al. | |
| 7,826,902 B2 | 11/2010 | Stone et al. | |
| 7,848,802 B2 | 12/2010 | Goetz et al. | |
| 2004/0034394 A1 | 2/2004 | Woods et al. | |
| 2004/0044279 A1 | 3/2004 | Lewin et al. | |
| 2004/0106916 A1 | 6/2004 | Quaid et al. | |
| 2004/0199216 A1 | 10/2004 | Lee et al. | |
| 2004/0267330 A1 | 12/2004 | Lee et al. | |
| 2005/0060001 A1 | 3/2005 | Singhal et al. | |
| 2005/0060009 A1 | 3/2005 | Goetz | |
| 2005/0070781 A1 | 3/2005 | Dawant et al. | |
| 2005/0171587 A1 | 8/2005 | Daglow et al. | |
| 2006/0017749 A1 | 1/2006 | McIntyre et al. | |
| 2006/0020292 A1 | 1/2006 | Goetz et al. | |
| 2006/0094951 A1 | 5/2006 | Dean et al. | |
| 2006/0235472 A1 | 10/2006 | Goetz et al. | |
| 2006/0259079 A1 | 11/2006 | King | |
| 2006/0259099 A1* | 11/2006 | Goetz et al. | 607/66 |
| 2007/0017749 A1 | 1/2007 | Dold et al. | |
| 2007/0043268 A1 | 2/2007 | Russell | |
| 2007/0049817 A1 | 3/2007 | Preiss et al. | |
| 2007/0083104 A1 | 4/2007 | Butson et al. | |
| 2007/0123953 A1* | 5/2007 | Lee et al. | 607/48 |
| 2007/0129769 A1 | 6/2007 | Bourget et al. | |
| 2007/0156186 A1 | 7/2007 | Lee et al. | |
| 2007/0162086 A1 | 7/2007 | DiLorenzo | |
| 2007/0185544 A1 | 8/2007 | Dawant et al. | |
| 2007/0191912 A1 | 8/2007 | Fischer et al. | |
| 2007/0203450 A1 | 8/2007 | Berry | |
| 2007/0203538 A1 | 8/2007 | Stone et al. | |
| 2007/0203539 A1 | 8/2007 | Stone et al. | |
| 2007/0203540 A1 | 8/2007 | Goetz et al. | |
| 2007/0203541 A1 | 8/2007 | Goetz et al. | |
| 2007/0203543 A1 | 8/2007 | Stone et al. | |
| 2007/0203544 A1 | 8/2007 | Goetz et al. | |
| 2007/0203545 A1 | 8/2007 | Stone et al. | |
| 2007/0203546 A1 | 8/2007 | Stone et al. | |
| 2007/0213789 A1 | 9/2007 | Nolan et al. | |
| 2007/0213790 A1 | 9/2007 | Nolan et al. | |
| 2007/0244519 A1 | 10/2007 | Keacher et al. | |
| 2007/0245318 A1 | 10/2007 | Goetz et al. | |
| 2007/0255321 A1 | 11/2007 | Gerber et al. | |
| 2007/0255322 A1 | 11/2007 | Gerber et al. | |
| 2007/0276441 A1 | 11/2007 | Goetz | |
| 2007/0282189 A1 | 12/2007 | Dan et al. | |
| 2007/0288064 A1 | 12/2007 | Butson et al. | |
| 2008/0027514 A1 | 1/2008 | DeMulling et al. | |
| 2008/0071150 A1 | 3/2008 | Miesel et al. | |
| 2008/0081982 A1 | 4/2008 | Simon et al. | |
| 2008/0086451 A1* | 4/2008 | Torres et al. | 707/3 |
| 2008/0103533 A1 | 5/2008 | Patel et al. | |
| 2008/0123922 A1 | 5/2008 | Gielen et al. | |
| 2008/0141217 A1 | 6/2008 | Goetz et al. | |
| 2008/0154340 A1 | 6/2008 | Goetz et al. | |
| 2008/0163097 A1 | 7/2008 | Goetz et al. | |
| 2008/0183256 A1 | 7/2008 | Keacher | |
| 2008/0215118 A1 | 9/2008 | Goetz et al. | |
| 2008/0269588 A1 | 10/2008 | Csavoy et al. | |
| 2008/0300654 A1 | 12/2008 | Lambert et al. | |
| 2009/0082640 A1 | 3/2009 | Kovach et al. | |
| 2009/0082829 A1 | 3/2009 | Panken et al. | |
| 2009/0112289 A1 | 4/2009 | Lee et al. | |
| 2009/0149917 A1 | 6/2009 | Whitehurst et al. | |
| 2009/0196471 A1 | 8/2009 | Goetz et al. | |
| 2009/0196472 A1 | 8/2009 | Goetz et al. | |
| 2009/0198306 A1 | 8/2009 | Goetz et al. | |
| 2009/0204192 A1 | 8/2009 | Carlton et al. | |
| 2009/0276008 A1 | 11/2009 | Lee et al. | |
| 2009/0281595 A1 | 11/2009 | King et al. | |
| 2009/0281596 A1 | 11/2009 | King et al. | |
| 2009/0287271 A1 | 11/2009 | Blum et al. | |
| 2009/0287272 A1 | 11/2009 | Kokones et al. | |
| 2009/0287273 A1 | 11/2009 | Carlton et al. | |
| 2009/0287467 A1 | 11/2009 | Sparks et al. | |
| 2009/0299164 A1 | 12/2009 | Singhal et al. | |
| 2009/0299165 A1 | 12/2009 | Singhal et al. | |
| 2009/0299380 A1 | 12/2009 | Singhal et al. | |
| 2010/0010646 A1 | 1/2010 | Drew et al. | |
| 2010/0023130 A1 | 1/2010 | Henry et al. | |
| 2010/0049276 A1 | 2/2010 | Blum et al. | |
| 2010/0049280 A1 | 2/2010 | Goetz | |
| 2010/0064249 A1* | 3/2010 | Groetken | 715/781 |
| 2011/0191275 A1 | 8/2011 | Lujan et al. | |

(56) References Cited

U.S. PATENT DOCUMENTS

2012/0207378 A1* 8/2012 Gupta et al. ............. 382/134
2012/0229468 A1* 9/2012 Lee et al. ............. 345/440

FOREIGN PATENT DOCUMENTS

| WO | 2007/097859 A1 | 8/2007 |
| WO | 2007/097861 A1 | 8/2007 |
| WO | 2007/100427 A1 | 9/2007 |
| WO | 2007/100428 A1 | 9/2007 |
| WO | 2007/112061 A2 | 10/2007 |
| WO | 2010/120823 A2 | 10/2010 |
| WO | 2011/139779 A1 | 11/2011 |
| WO | 2011/159688 A2 | 12/2011 |

OTHER PUBLICATIONS

Butson et al., "Patient-Specific Analysis of the Volume of Tissue Activated During Deep Brain Stimulation," Neuroimage 34, 2007, pp. 661-670.

Butson et al., "Role of Electrode Design on the Volume of Tissue Activated During Deep Brain Stimulation," Journal of Neural Engineering, Mar. 1, 2006, vol. 3, No. 1, pp. 1-8.

Butson et al., "StimExplorer: Deep Brain Stimulation Parameter Selection Software System," Acta Neurochirugica, Jan. 1, 2007, vol. 97, No. 2, pp. 569-574.

Miocinovic et al., "Cicerone: Stereotactic Neurophysiological Recording and Deep Brain Stimulation Electrode Placement Software System," Acta Neurochirurgica Suppl., Jan. 1, 2007, vol. 97, No. 2, pp. 561-567.

Schmidt et al., "Sketching and Composing Widgets for 3D Manipulation," Eurographics, Apr. 2008, vol. 27, No. 2, pp. 301-310.

Izad, Olivier, "Computationally Efficient Method in Predicating Axonal Excitation," Dissertation for Masters Degree, Department of Biomedical Engineering, Case Western Reserve University, May 2009, 144 pages.

Jaccard, Paul, "Étude comparative de la distribution florale dans une portion odes Aples et des Jura," Bulletin de la Société Vaudoise des Sciences Naturelles (1901), vol. 37, pp. 547-579.

Dice, Lee R., "Measures of the Amount of Ecologic Association Between Species," Ecology 26(3) (1945), pp. 297-302. doi:10.2307/1932409, http://jstor.org/stable/1932409.

Rand, W.M., "Objective criteria for the evaluation of clustering methods," Journal of the American Statistical Association (American Statistical Association) 66 (336) (1971), pp. 846-850, doi:10.2307/2284239, http://jstor.org/stable/2284239.

Hubert, Lawrence et al., "Comparing partitions," Journal of Classification 2(1) (1985), pp. 193-218, doi:10.1007/BF01908075.

Cover, T.M. et al., "Elements of information theory," (1991) John Wiley & Sons, New York, NY, pp. 1-542.

Meila, Marina, "Comparing Clusterings by the Variation of Information," Learning Theory and Kernel Machines (2003), pp. 173-187.

European Patent Office, International Search Report in International Application No. PCT/US2012/053344, dated Nov. 26, 2012, 8 pages.

European Patent Office, International Search Report and the Written Opinion of the International Searching Authority in International Application No. PCT/US2012/050175, dated Oct. 26, 2012, 15 pages.

European Patent Office, PCT Search Report from PCT/US09/03041, dated Aug. 20, 2009, 7 pages.

European Patent Office, International Search Report in International Application No. PCT/US2012/050181, dated Jan. 3, 2013, 7 pages.

Euopean Patent Office, International Search Report and the Written Opinion in International Application No. PCT/US2012/050170, dated Oct. 5, 2012, 15 pages.

Ericsson, A. et al., "Construction of a patient-specific atlas of the brain: Application to normal aging," Biomedical Imaging: From Nano to Macro, ISBI 2008, 5th IEEE International Symposium, May 14, 2008, pp. 480-483.

Kaikai Shen et al., "Atlas selection strategy using least angle regression in multi-atlas segmentation propagation," Biomedical Imaging: From Nano to Macro, 2011, 8th IEEE International Symposium, ISBI 2011, Mar. 30, 2011, pp. 1746-1749.

Liliane Ramus et al, "Assessing selection methods in the context of multi-atlas based segmentation," Biomedical Imaging: From Nano to Macro, 2010 IEEE International Symposium, Apr. 14, 2010, pp. 1321-1324.

Olivier Commowick et al., "Using Frankenstein's Creature Paradigm to Build a Patient Specific Atlas," Sep. 20, 2009, Medical Image Computing and Computer-Assisted Intervention, pp. 993-1000.

Lotjonen J.M.P. et al, "Fast and robust multi-atlas segmentation of brain magnetic resonance images," NeuroImage, Academic Press, vol. 49, No. 3, Feb. 1, 2010, pp. 2352-2365.

European Patent Office, International Search Report and Written Opinion in International Application No. PCT/US2012/030700, dated Feb. 27, 2013, 9 pages.

Sanchez Castro et al., "A cross validation study of deep brain stimulation targeting: From experts to Atlas-Based, Segmentation-Based and Automatic Registration Algorithms," IEEE Transactions on Medical Imaging, vol. 25, No. 11, Nov. 1, 2006, pp. 1440-1450.

European Patent Office, PCT Search Report from PCT/US09/03017, dated Aug. 3, 2009, 7 pages.

European Patent Office, PCT Search Report from PCT/US09/03038, dated Oct. 8, 2009, 9 pages.

European Patent Office, PCT Search Report from PCT/US09/03040, dated Aug. 13, 2009, 7 pages.

European Patent Office, PCT Search Report from PCT/US09/03049, dated Jan. 26, 2010, 8 pages.

European Patent Office, partial International Search Report in International Application No. PCT/US2012/030701, dated Feb. 15, 2013, 7 pages.

European Patent Office, partial International Search Report in International Application No. PCT/US2012/030705, dated Mar. 6, 2013, 7 pages.

Siegel, Ralph M. et al., "Spatiotemporal dynamics of the functional architecture for gain fields in inferior parietal lobule of behaving monkey," Cerebral Cortex, New York, NY, vol. 17, No. 2, Feb. 2007, pp. 378-390.

Klein, A. et al., "Evaluation of 14 nonlinear deformation algorithms applied to human brain MRI registration," NeuroImage, Academic Press, Orlando, FL, vol. 46, No. 3, Jul. 2009, pp. 786-802.

European Patent Office, International Search report and Written Opinion in PCT application No. PCT/US12/050174, dated Mar. 6, 2013, 20 pages.

European Patent Office, International Search Report and Written Opinion in International Application No. PCT/US2012/050187, dated Feb. 27, 2013, 9 pages.

* cited by examiner (a)

STIMULATION LEADWIRE AND VOLUME OF ACTIVATION CONTROL AND DISPLAY INTERFACE

CROSS-REFERENCE TO RELATED APPLICATIONS

The present application claims priority to U.S. Provisional Patent Application Ser. No. 61/549,079 filed Oct. 19, 2011, the content of which is hereby incorporated by reference herein in its entirety. This application is also related to subject matter of U.S. Provisional Patent Application Ser. No. 61/521,572 filed Aug. 9, 2011, the content of which is hereby incorporated by reference in its entirety.

FIELD OF THE INVENTION

The present invention pertains to quantification and/or control of overlap of an estimated volume of tissue activated by a stimulation over a target volume of stimulation. Embodiments of the present invention pertain to control and display of graphical user interfaces via which to control (actual or simulated) a stimulation leadwire implanted in a patient and via which to view actual and/or estimated effects of a parameter set applied to the leadwire, in comparison with a target volume of activation. Aspects of the present invention pertain to leadwires and controls and displays thereof as described in U.S. patent application Ser. No. 12/454,330, filed May 15, 2009 ("the '330 application"), U.S. patent application Ser. No. 12/454,312, filed May 15, 2009 ("the '312 application"), U.S. patent application Ser. No. 12/454,340, filed May 15, 2009 ("the '340 application"), U.S. patent application Ser. No. 12/454,343, filed May 15, 2009 ("the '343 application"), U.S. patent application Ser. No. 12/454,314, filed May 15, 2009 ("the '314 application"), U.S. Prov. Pat. App. Ser. No. 61/468,884, filed Mar. 29, 2011 ("the '884 application"), U.S. Prov. Pat. App. Ser. No. 61/468,887, filed Mar. 29, 2011 ("the '887 application"), U.S. Prov. Pat. App. Ser. No. 61/468,891, filed Mar. 29, 2011 ("the '891 application"), U.S. Prov. Pat. App. Ser. No. 61/468,897, filed Mar. 29, 2011 ("the '897 application"), U.S. Prov. Pat. App. Ser. No. 61/468,901, filed Mar. 29, 2011 ("the '901 application"), and U.S. Prov. Pat. App. Ser. No. 61/521,626, filed Aug. 9, 2011 ("the '626 application"), the content of each of which is hereby incorporated by reference herein in their entireties.

BACKGROUND INFORMATION

Electrical stimulation of an anatomical region, e.g., deep brain stimulation (DBS), such as of the thalamus or basal ganglia, or spinal cord stimulation (SCS) therapy, is a clinical technique for the treatment of disorders such as essential tremor, Parkinson's disease (PD), and other physiological disorders. DBS may also be useful for traumatic brain injury and stroke. Pilot studies have also begun to examine the utility of DBS for treating dystonia, epilepsy, and obsessive-compulsive disorder.

A stimulation procedure, such as DBS, typically involves first obtaining preoperative images, e.g., of the patient's brain, such as by using a computed tomography (CT) scanner device, a magnetic resonance imaging (MRI) device, or any other imaging modality. This sometimes involves first affixing to the patient's skull spherical or other fiducial markers that are visible on the images produced by the imaging modality. The fiducial markers help register the preoperative images to the actual physical position of the patient in the operating room during the later surgical procedure.

After the preoperative images are acquired by the imaging modality, they are then loaded onto an image-guided surgical (IGS) workstation, and, using the preoperative images displayed on the IGS workstation, a neurosurgeon can select a target region, e.g., within the brain, an entry point, e.g., on the patient's skull, and a desired trajectory between the entry point and the target region. The entry point and trajectory are typically carefully selected to avoid intersecting or otherwise damaging certain nearby critical structures or vasculature, e.g., of the brain.

In the operating room, the physician marks the entry point on the patient's skull, drills a burr hole at that location, and affixes a trajectory guide device about the burr hole. The trajectory guide device includes a bore that can be aimed to obtain the desired trajectory to the target region. After aiming, the trajectory guide is locked to preserve the aimed trajectory toward the target region. After the aimed trajectory has been locked in using the trajectory guide, a microdrive introducer is used to insert the surgical instrument along the trajectory toward the target region, e.g., of the brain. The surgical instrument may include, among other things, a recording electrode leadwire, for recording intrinsic electrical signals, e.g., of the brain; a stimulation electrode leadwire, for providing electrical energy to the target region, e.g., of the brain; or associated auxiliary guidewires or guide catheters for steering a primary instrument toward the target region, e.g., of the brain.

The stimulation electrode leadwire, which typically includes multiple closely-spaced electrically independent stimulation electrode contacts, is then introduced to deliver the therapeutic stimulation to the target region, e.g., of the brain. The stimulation electrode leadwire is then immobilized, such as by using an instrument immobilization device located at the burr hole entry, e.g., in the patient's skull, in order for the stimulation therapy to be subsequently performed.

The subthalamic nucleus (STN) represents the most common target for DBS technology. Clinically effective STN DBS for PD has typically used electrode contacts in the anterior-dorsal STN. However, STN DBS exhibits a low threshold for certain undesirable side effects, such as tetanic muscle contraction, speech disturbance and ocular deviation. Highly anisotropic fiber tracks are located about the STN. Such nerve tracks exhibit high electrical conductivity in a particular direction. Activation of these tracks has been implicated in many of the DBS side effects. However, there exists a limited understanding of the neural response to DBS. The three-dimensional (3D) tissue medium near the DBS electrode typically includes both inhomogeneous and anisotropic characteristics. Such complexity makes it difficult to predict the particular volume of tissue influenced by DBS.

After the immobilization of the stimulation electrode leadwire, the actual stimulation therapy is often not initiated until after a time period of about two-weeks to one month has elapsed. This is due primarily to the acute reaction of the tissue to the introduced electrode leadwire (e.g., the formation of adjacent scar tissue), and stabilization of the patient's disease symptoms. At that time, a particular one or more of the stimulation electrode contacts is selected for delivering the therapeutic stimulation, and other stimulation parameters are adjusted to achieve an acceptable level of therapeutic benefit.

A system and method can estimate stimulation volumes, and display models of a patient anatomy and/or a stimulation leadwire, via which to graphically identify the estimated stimulation volumes and how they interact with various regions of the patient anatomy, for example, as described in the '330, '312, '340, '343, and '314 applications.

The systems and methods can be used to explore target regions of stimulation and stimulation therapies to determine which therapy regimen is best suited for a particular patient or group of patients. The system is configured to display a graphical user interface via which to visually indicate a position of the leadwire in the patient anatomy and/or an actual or estimated effect of stimulation parameters applied to the stimulation leadwire, for example in the form of a volume of estimated activation (VOA), and/or via which to modify the parameter settings to be applied to the stimulation leadwire.

DETAILED DESCRIPTION

Example embodiments of the present invention are directed to quantifying a degree to which an estimated volume of activation (VOA) matches another obtained volume, such as, for example, a specified anatomical volume such as the sub-thalamic nucleus (STN), another VOA such as one which corresponds to another set of stimulation parameters, a side effect volume, and a target volume of activation, e.g., that is set with respect to a particular stimulation therapy. The example embodiments discussed below are discussed with respect to degree of match to a target volume or side effect volume, but the discussion below similarly applies to other volume types. Example embodiments of the present invention also pertain to selection of a best VOA in accordance with a quantified similarity between each of a plurality of VOAs and another volume, such as the target volume of activation.

For example, a target volume can be manually or automatically obtained, e.g., as described in the '330, '312, '340, '343, '314, and '626 applications (and can be output using systems described therein). The target volume can be of a region of a patient's brain for DBS or other anatomical region, e.g., for SCS. A VOA can be calculated and/or set as described for example in the '330, '312, '340, '343, '314, and '626 applications (and can be output using systems described therein).

The system is configured to compare a VOA corresponding to a set of stimulation parameters, such as pulse width and/or voltage amplitude of one or more electrodes of an implanted leadwire, to the target volume, and quantify the similarity between the VOA and target volume, e.g., in the form of a degree of overlap of the volumes and/or spillover of the VOA beyond the boundaries of the target volume.

The following notations will be used below in discussions of target volumes and VOAs: V=VOA; and T=target volume of activation, where the VOA refers to a volume of tissue to be activated by application of stimulation parameters to a leadwire implanted in a patient, for example for spinal cord or deep brain stimulation, and the target volumes are those targeted to be activated. The VOA refers to an actually stimulated region or a region estimated to be activated in view of the applied stimulation parameters. Additionally, side effect volumes of activation refer to volumes where a side effect occurs or is estimated to occur because of the stimulation.

According to example embodiments of the present invention, a system and method includes consideration by a computer processor of one or more, e.g., all, of four kinds of subsets, including (1) V intersect T (i.e., the area where the target volume and the VOA overlap), (2) V intersect T complement (where T complement is everything in a considered anatomical region that is not within the target volume), (3) V complement intersect T (i.e., the area of the target volume with which the VOA does not overlap), and (4) V complement intersect T complement (i.e., the area of the considered anatomical region in which neither the VOA nor the target volume fall). According to an example embodiment of the present invention, the system uses quantities of these four metrics to describe everything about two data sets, i.e., a data set corresponding to the VOA and a data set corresponding to the target volume. Ideally V should agree with T, and their complements should agree with each other.

According to an example embodiment of the present invention, based on the Jaccard index, the system is configured to calculate $$\frac{V \cap T}{V \cup T}, \quad \text{(eq. 1)}$$

where $\cap$ symbolizes the intersection and $\cup$ symbolizes the union. That is, V∩T refers to the area that is common to both V and T, and V∪T refers to the combination of the area that is within V and not within T, the area that is within T and not within V, and the are in which T and V overlap.

Where the result of the calculation is 1, there is perfect agreement between T and V. Where the result of the calculation if 0, there is no agreements between T and V, i.e., this occurs where V∩T=0. A result that falls between 0 and 1 characterizes a degree of agreement between the volumes that is greater than no agreement but less than perfect agreement.

According to an example embodiment of the present invention, the system is configured to output the result of the calculation as a characterization of the degree of agreement between the target volume and VOA. For example, in a predefined mode of the system, as the user modifies stimulation settings, the system is configured to responsively update a score displayed in a user interface.

For any voxel within the considered anatomical space, if the voxel is within both T and V, the voxel may be referred to herein as a true positive; if the voxel is within both T compliment and V, the voxel may be referred to herein as a false positive; if the voxel is within both T and V complement, the voxel may be referred to herein as a false negative; and if the voxel is within both T complement and V complement, the voxel may be referred to herein as a true negative. Therefore, for example, eq. 1 can be expressed as $$\frac{\text{true\_positives}}{\text{true\_positives} + \text{false\_positives} + \text{false\_negatives}}.$$

However, eq. 1 does not quantify or characterize true negatives. That is, eq. 1 indicates a ratio of the overlapping regions to the combination of regions within either of the target volume and the VOA, but its result is not affected by a consistency of area not falling within the considered volumes.

In an alternative example embodiment, based on the Rand index, the system is further configured to quantify a consistency between the target volume and VOA in a manner by which the quantification reflects true negatives. According to an example, the system is configured to calculate $$\frac{[V \cap T] + [V^c \cap T^c]}{[V \cup T] + [V^c \cap T^c]}, \quad (\text{eq. 2})$$

where $V^c$ is the area of V complement and $T^c$ is the area of T complement. Compared to eq. 1, eq. 2 adds true negative to both the numerator and denominator. Specifically, the numerator includes all voxels in which V and T agree and all voxels in which $V^C$ and $T^C$ agree; and the denominator includes all voxels in the considered area.

Where the result of the calculation using eq. 2 is 1, there is perfect agreement between T and V, and their compliments. However, where there is no agreement between T and V, the result is usually not 0 because there usually is at least some agreement between $V^C$ and $T^C$. Instead, where there is no agreement between T and V, the result varies depending on the area being considered, such that the greater the area being considered (and thus the greater $V^c \cap T^c$), the greater the result. Similarly, where there is some agreement between T and V and also some agreement between $V^c$ and $T^c$, the result reflects both the agreement between T and V and also the agreement between $V^c$ and $T^c$. According to an example embodiment of the present invention, the system is configured to output the result of the calculation as a characterization of the degree of agreement between the target volume and VOA and between their compliments.

An embodiment using eq. 2 is advantageous over an embodiment in which eq. 1 is used because it is advantageous to assign a greater value for those instances where there is more overlap of the complement areas. On the other hand, an embodiment in which eq. 1 is used is advantageous because of the simplicity of the characterization using a value between 0 and 1 to indicate a degree of overlap.

Figure 1:
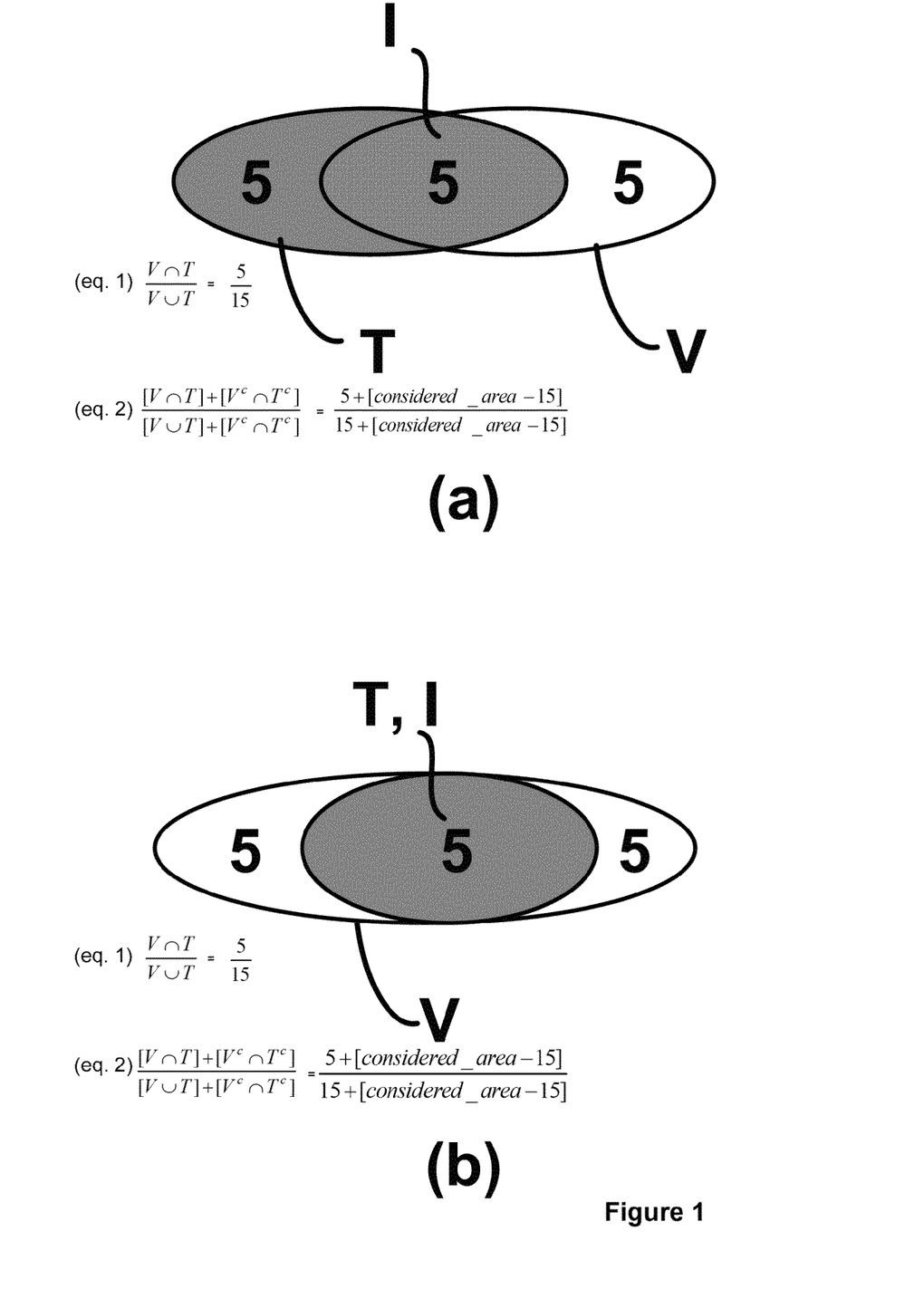
FIG. 1 illustrates representations of different scenarios of VOA and target region overlap and corresponding score function results, according to example embodiments of the present invention.

However, the embodiments discussed above using eq. 1 or eq. 2 each provides for two very different scenarios a same respective score. For example, the two scenarios can be as shown in FIG. 1. In the first scenario represented by part (a) of FIG. 1, V=10, T=10, and I=5, where 'I' is the intersection of T and V. In the second scenario represented by part (b) of FIG. 1, V=15, T=5, and I=5, such that T is completely included within V. Applying eq. 1 to each of the two scenarios provides a result of 5/15. (Further in this regard, the denominator in the first scenario is 15 even though each of V and T is 10, because V and T overlap at portion I, and portion I is counted just once. Similarly, the denominator in the second scenario is 15 even though T is 5 and V is 15, because T corresponds to I and therefore completely overlaps V at portion I, and portion I is counted just once. Stated otherwise, in the second scenario, T can be ignored with respect to the denominator.)

Similarly, applying eq. 2 to each of the two scenarios provides a result of $$\frac{5 + [\text{considered\_area} - 15]}{15 + [\text{considered\_area} - 15]}.$$

In this regard, eq. 2 differs from eq. 1 in that eq. 2 further considers the true negative area $V^c \cap T^c$, which is all of the considered area except for any area that falls within any of T, V, and I (which is 15 in both of the first and second scenarios, i.e., the true negatives in both the first and second scenarios are the same).

That eq. 1 and eq. 2 do not differentiate between the first and second scenarios, despite that so much less of V is external to T in the first scenario than the second scenario, and despite that so much more of T is external to V in the first scenario than the second scenario, indicates that information is lost by these equations, i.e., information representative of such differences.

Figure 2:
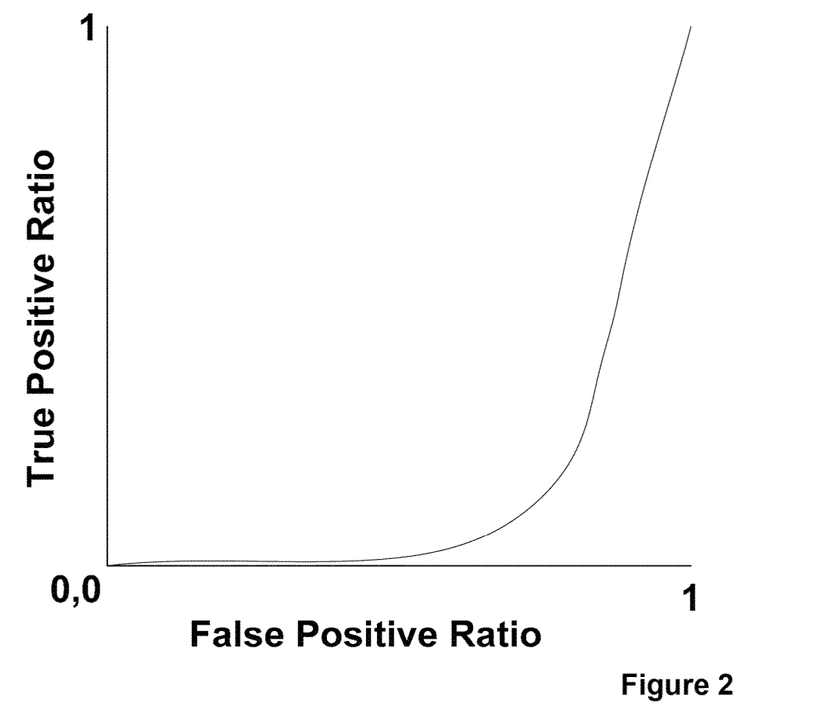
FIG. 2 is a graph plotting false positive scores against true positive scores of VOA to target region overlap, calculated for various stimulation settings, according to an example embodiment of the present invention.

Accordingly, in an example embodiment of the present invention, the system and method quantifies a correspondence of V to T by plotting values representative of the correspondence in a receiver operating characteristic (ROC) graph. FIG. 2 shows an example ROC graph. For example, the system calculates a true positive value and a false positive value, and plots in the ROC graph a point representative of the intersection of the calculated values, which intersection point is a quantification of the overlap of the VOA and the target volume. For example, the abscissa can be set to be representative of the false positive value and the ordinate can be set to be representative of the true positive value, as shown in FIG. 2. Such points have been plotted in the graph of FIG. 2 for a plurality of stimulation settings to obtain a curve, i.e., a ROC curve.

According to an example embodiment of the present invention, the true positive value is $$\frac{V \cap T}{T}$$

and the false positive value is $$\frac{V \cap T^c}{T^c},$$

such that the true positive and false positive values will always fall at one of, or between, 0 and 1.

Generally speaking, as the value of a stimulation parameter, e.g., a stimulation amplitude or pulse width, is increased, the size of the VOA increases. Therefore, often the increase of the value of the stimulation parameter causes the overlap of the VOA over the area of the of the target volume to increase, but also causes the overlap of the VOA over $T^c$ to increase. The ROC curve can be used to find a good balance between activating area belonging to the target volume and avoiding activation of area belonging to the complement of the target volume. For example, parameters corresponding to point 1,1 on the ROC curve (where V encompasses all of T and $T^c$) are usually undesirable, and parameters corresponding to point 0,0 on the ROC curve (where V does not encompass any of $T^c$, but also does not encompass any of T) are also usually undesirable. Accordingly, a point on the ROC curve that falls somewhere between points 0,0 and 1,1, and the stimulation parameters corresponding to that point, can be selected as candidate parameters.

The ROC curve often includes a knee where the curve begins to slope more drastically towards 1,1. Accordingly, the user viewing the ROC curve output by the system can select a point on the ROC to select ideal stimulation parameters. For example, in an example embodiment, the ROC curve is presented in a user interface in which the user is able to use an input device to select a point on the ROC curve, to which selection the system is configured to respond by selecting the parameters corresponding to said selected point, as ideal stimulation parameter settings, either to be output as a suggestion to the clinician or to automatically apply to the implanted leadwire. For example, the user can select the point which appears to the user as most closely corresponding to the knee.

In an example embodiment, the system outputs a graphical representation of the VOA in an anatomical atlas space and/or overlapping a representation of the implanted leadwire and/or overlapping the target volume. The clinician can use the output information to determine whether to use the suggested parameter settings or to tweak the parameter settings until the clinician finds favorable settings.

Thus, according to an example embodiment, the system outputs the ROC graph, including the plotted curve, and the clinician can manually select a point within the curve, in order to select the corresponding settings. The system can responsively output the corresponding settings and/or set the implanted leadwire according to the corresponding settings, as discussed above, and/or can output a representation of the corresponding volume as discussed above.

The curve can be constructed of points corresponding to many different stimulation parameter combinations, including different combinations of active electrodes, different amplitude settings for the various electrodes, different pulse widths, etc. The system plots the points, and a knee point, and its corresponding parameters, can be selected, as discussed above. Additionally, different curves can be plot for different selected stable settings, i.e., for each of the plotted curves, the value(s) of one or more respective ones of the stimulation parameters are the same for all plotted values, the values of other respective parameters being changed. For example, different curves can be plotted for different leadwire positions, i.e., the leadwire position is the same for all plotted points of such a curve; or different curves can be plotted for different pulse widths, i.e., the pulse width is the same for all plotted points of the curve; etc. Any parameter can be selected as a stable parameter whose value remains the same for all plotted values of the respective curve.

In an example embodiment, different curves can be plotted for different patients. Thus, different points can be selected for different patients. This can be advantageous because the curves can be drastically different for different patients. For example, it can occur that for a first patient, the true positive and false positive values are the same for many or all parameter settings, such that the ROC curve is actually approximately a straight line having a slope of 1, so that the ROC curve for the patient provides no reason to increase the VOA, because the overlap with $T^c$ is increased at the same rate as the overlap with T. On the other hand, the ROC curve plotted for another patient can include a point at which the true positive begins to increase at a faster rate than the false positive until an approximate leveling off of the slope. A different set of parameter settings would therefore be selected for the second patient, due to the gain achieved by increasing the parameter setting to the curve point where this leveling off occurs.

Thus, the ROC curve(s) both quantify the T and V overlap and help with selection of optimal parameter settings.

According to an alternative example embodiment of the present invention, the system applies a mutual information formula to generate a score representative of the degree to which V corresponds to T. In this regard, the probability that a random selected area, e.g., voxel, belongs to V is V/[total considered area]; the probability that it belongs to T is T/[total considered area]; the probability that it belongs to $V^c$ is $V^c$/[total considered area]; the probability that it belongs to $T^c$ is $T^c$/[total considered area]; and the probability that it belongs to I is I/[total considered area]. However, for example, given information that, for example, the random selected area belongs to T, can change the probability that it belongs to V. For example, if T=10 and I=5, then, with such given information, the probability that it belongs to V is 0.5. The mutual information formula quantifies such effects on probabilities given the overlaps of the various considered areas (T, V, $T^c$, $V^c$). That is, it quantifies how information concerning one of the considered areas affects the probabilities of the area belonging to others of the considered areas, and it characterizes how the partitioning of the area into T and $T^c$ reflects the partitioning of the area into V and $V^c$, and vice versa.

In the following, the braces { } indicate that reference is being made to the partitions (the data set representing the volume and its complement), whereas the letters V and T, without the braces, indicates that reference is being made to the volumes themselves.

Formally, P(V) can be defined as the probability that a randomly chosen voxel belongs in V, P(T) can be defined as the probability that a randomly chosen voxel belongs in T, $P(V^c)$ can be defined as the probability that a randomly chosen voxel belongs in $V^c$, and $P(T^c)$ can be defined as the probability that a randomly chosen voxel belongs in $T^c$.

Entropies (measures of unpredictability) for the partitions: {V} (i.e., the set of V and $V^c$), {T} (i.e., the set of T and $T^c$), and {V,T} (i.e., the combination of the sets of V, $V^c$, T, and $T^c$) can then be defined as:

$$H(\{V\}) = -P(V)\log_e(P(V)) - P(V^c)\log_e(P(V^c)) \quad \text{(eq. 3)};$$

$$H(\{T\}) = -P(T)\log_e(P(T)) - P(T^c)\log_e(P(T^c)) \quad \text{(eq. 4); and}$$

$$H(\{V,T\}) = -P(V,T)\log_e(P(V,T)) - P(V,T^c)\log_e(P(V,T^c)) - P(V^c,T)\log_e(P(V^c,T)) - P(V^c,T^c)\log_e(P(V^c,T^c)) \quad \text{(eq. 5)}.$$

Mutual information can then be computed, according to an example embodiment of the present invention, as MI=H({T})+H({V})−H({V,T}) (eq. 6). In an example embodiment, the computed mutual information value is output as a quantification of the correspondence between the target volume and the VOA.

In an example embodiment, the system calculates a normalized mutual information, which has a value of one of, or between, 0 and 1 or a different definition dependent maximum value that is less than 1. The normalized mutual information value can be calculated in a number of alternative ways. For example, the normalized mutual information value can be calculated as $$\frac{2MI}{H(\{V\}) + H(\{T\})}. \quad \text{(eq. 7)}$$

The resulting value indicates the degree of correspondence between the VOA and the target volume, where 0 represents no overlap, and 1 or a different definition dependent maximum value less than 1 corresponds to perfect overlap.

According to an alternative example embodiment, the system calculates the sum of the entropy of the two partitions ([T, $T^c$] and [V, $V^c$]) minus twice the mutual information, i.e., $H(\{T\})+H(\{V\})-2MI$ (eq. 8), which results in a score that can be normalized to a value at one of, or between, 0 and 1. This quantity measures the extent to which knowledge of one partition reduces uncertainty about the other partition and is known as the variation of information (see Marina Meila, "Comparing Clusterings by the Variation of Information," Learning Theory and Kernel Machines: 173-187 (2003), which is incorporated by reference herein in its entirety). Note that variation of information may also be written as $H(V|T)+H(T|V)$, i.e., the sum of the entropy of the T partition given the V partition and the entropy of the V partition given the T partition.

As discussed in, for example, the '330, '312, '340, '343, '314, and '626 applications, certain anatomical regions, referred to herein as side effect regions, can be set as regions in which stimulation is preferably avoided. While a VOA might closely match a target volume, it can also overlap a portion or all of one or more of such side effect regions. Selecting stimulation parameters can therefore include a balancing between meeting a target region and avoiding to some extent such side effect regions. According to an example embodiment of the present invention, the system is configured to calculate a measure of a correspondence of a VOA to a target region and also to calculate a measure of a correspondence of the VOA to one or more side effect regions. Based on output of such measures, a user can select stimulation settings that provide a VOA that strikes a good balance between obtaining a good correspondence between the VOA and the target region and a weak correspondence between the VOA and the one or more side effect regions. For example, the system can calculate the correspondence between the VOA and the side effect regions using any of the methods described above, e.g., eq. 1, eq. 2, the ROC graph/curve, the mutual information formula, or the entropy formula.

According to an example embodiment of the present invention, the system plots the target overlap and side effect overlap scores for a plurality of stimulation settings in a shared graph space. For example, the abscissa can correspond to the sets of stimulation settings for which the scores have been calculated and the ordinate can correspond to the score, or vice versa. According to an example of this embodiment, the system is configured to connect the plotted target region scores to form a first curve and to connect the plotted side effect region scores to form a second curve. According to an example of this embodiment, the system is configured to graphically identify whether a plotted score is associated with the target region or with the side effect region. For example different colors, hatching, or size of the nodes and/or connecting lines can be used for differentiation. The user is thereby visually informed of the correspondence between target and side effect region overlap for the different settings. The user is then able to select those settings which the user determines provides the best trade-off between target region overlap and side effect region avoidance. For example, in an example embodiment, the system provides the integrated graph in a user interface in which the user is able to select a point within the graph corresponding to one of the sets of parameter settings. Responsive to such selection, the system is configured to display information regarding the selected settings, e.g., amplitude, pulse width, rate, electrode combination, etc.; and/or display the corresponding VOA, e.g., in spatial relation to the target region and/or side effect region(s), and/or in spatial relation to a graphical representation of the implanted leadwire, and/or in spatial relation to anatomical structures, e.g., atlas structures and/or medical image structures. Alternatively or additionally, the system responds to the selection by programming the implanted pulse generator (IPG) with the selected settings. Alternatively, the interface includes a separate selectable input element, in response to selection of which, the system programs the IPG with the selected settings.

According to the embodiment in which the ROC curves are plotted for the target and side effect region overlap, in an example embodiment, in order to visually indicate the correlation between the curves for the target region(s) and side effect region(s), the system plots the scores in a three-dimensional coordinate space, where a first axis corresponds to the false positive score, a second axis corresponds to the true positive score, and the third axis corresponds to the stimulation settings for which the scores were calculated. Alternatively, the system outputs a separate, e.g., two-dimensional, graph for each set of parameter settings for which the scores are calculated, where one of the axes corresponds to the false positive scores and another of the axes corresponds to the true positive scores, but where all plotted scores of the respective graph correspond to a single one of the sets of parameter settings. The user can then select the graph which includes those plotted points the user determines reflects the best trade-off between matching the target volume(s) and avoiding the side effect volume(s).

It is noted that there may be more than one target region. In an example embodiment, the system treats the multiple regions as multiple sub-regions of a single target region for which a respective score is calculated and output. Alternatively, the system calculates a single composite target region score based on the scores for the multiple target regions, e.g., an average of the scores. According to an example variant of this embodiment, the system differently weights different ones of the target regions. For example, one target region can be set as being more important than another target region, and the system therefore assigns a greater weight to the score calculated for the more important region. For example, different target regions may be associated with different therapeutic effects, which effect their importance. (The system can similarly calculate a single side effect region score based on scores calculated for multiple side effect regions. Further, different side effect regions can be differently weighted, e.g., because of the type or severity of the side effects with which they are associated.)

As noted above, in an example embodiment, separate scores are calculated and output for each of the target regions. Their scores can be plotted in a graph, one of whose axes corresponds to the sets of stimulation settings. The user can then select the settings providing the best balance between coverage of the multiple target regions. According to the embodiment in which an ROC graph is output, a three-dimensional graph may be output, where one of the axes corresponds to the sets of stimulation settings. Alternatively, a different graph can be output for each set of stimulation settings for which the calculations are made.

According to an example embodiment of the present invention, the system calculates for a set of stimulation settings a single score based on the scores calculated for the one or more target regions and the one or more side effect regions. For example, an average or weighted average of all of the scores can be calculated, e.g., where the side effect region scores are assigned a negative value and the target region scores are assigned a positive value. The different target and side effect regions can be weighted differently, as noted above. According to an embodiment in which the ROC graph is used, a single composite true positive score can be calculated and a single composite false positive score can be calculated for a single set of stimulation parameters, based on the overlap and/or spill of a plurality of target and side effect regions, where, for example, the side effect regions are assigned a negative value for their true positive scores and a positive value for their false positive scores and vice versa for the target regions. According to this embodiment as well, different regions can be differently weighted.

According to an example embodiment of the present invention, a system includes a processor that is configured to obtain one or more medical images, e.g., magnetic resonance image (MRI) or computed tomography (CT) image, of an anatomical region of a patient, and display the image(s) or an anatomical atlas conforming to the image(s) in a graphical user interface (GUI). The image can be one taken after implantation of a leadwire, such that the leadwire is displayed in the image. Alternatively (or additionally), a leadwire model can be superimposed by the processor over a part of the displayed image corresponding to the location of the leadwire in the anatomical region of the patient. In an example embodiment, the GUI includes controls for controlling stimulation parameters to be set for the electrodes (also referred to herein as "electrode contacts") of the leadwire (also referred to herein as "lead"), for actual programming of the leadwire to stimulate a portion of the displayed anatomical region of the patient and/or for simulation of such stimulation. In an example embodiment of the present invention, the processor is configured to provide in the GUI a legend that identifies, e.g., by color coding or hatching, various structures of the displayed image or atlas, to help the user better understand the relative positions of significant structures within the display, e.g., relative to the leadwire or one or more of the displayed anatomical structures.

Figure 3:
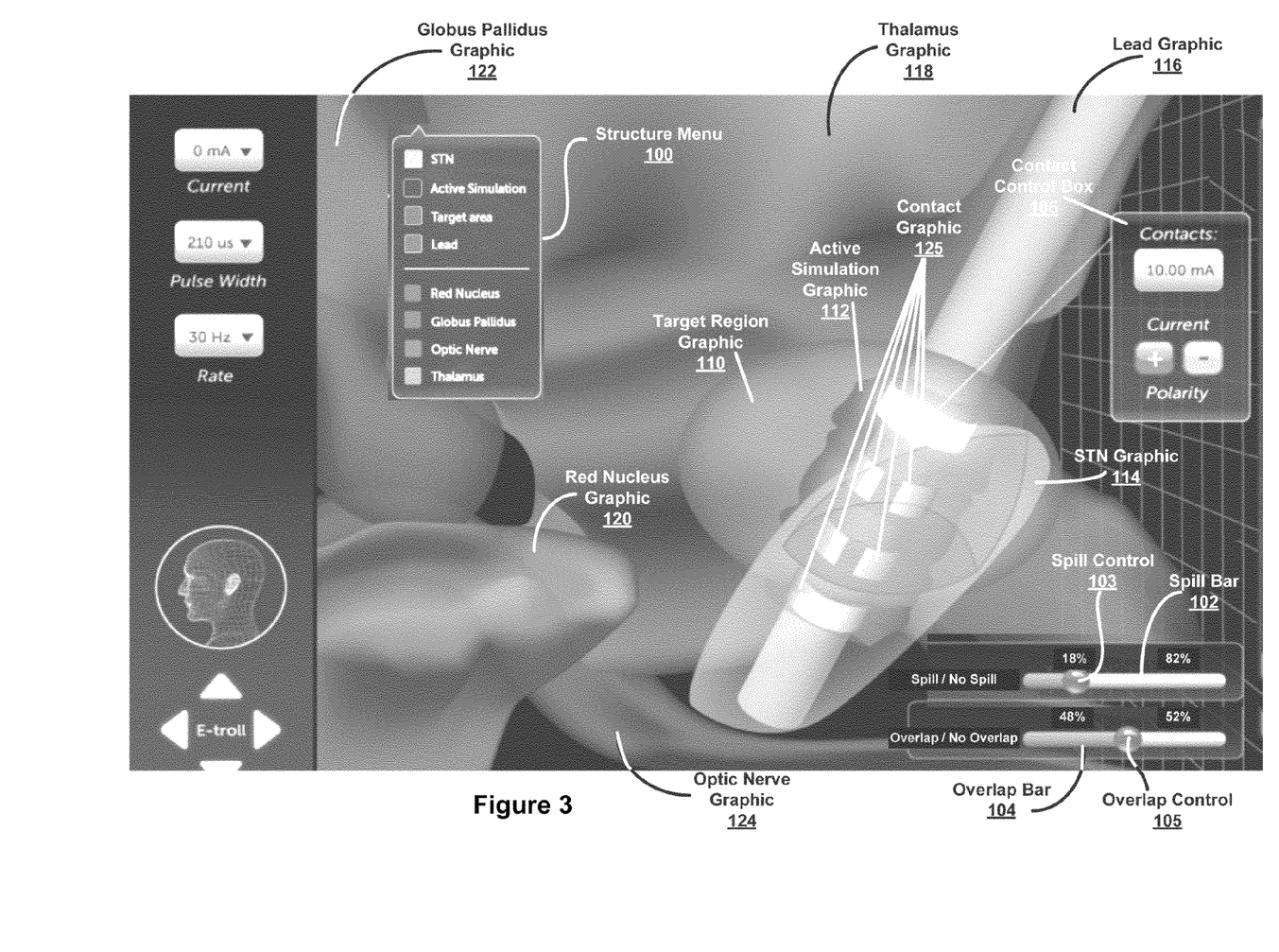
FIG. 3 is a screenshot of a graphical user interface for displaying anatomical, mechanical, electrical, and/or stimulation dependent components, and stimulation controls, according to an example embodiment of the present invention.

FIG. 3 shows a GUI according to an example embodiment of the present invention. The GUI includes a display of an atlas of a region of a patient's brain. The displayed atlas (and/or medical image) can be two dimensional or three dimensional. In FIG. 3, it is three dimensional. Although the features described with reference to FIG. 3 pertain to the brain, the features can similarly be provided with respect to any anatomical region of a patient. Additionally, while FIG. 3 shows an atlas of a brain that has been conformed to medical images of a user, the features can similarly be applied to the actual medical images, by overlaying the described controls and graphical elements over the medical images.

The displayed atlas includes representations of a plurality of anatomical structures. They include a sub-thalamic nucleus (STN) graphic 114, a thalamus graphic 118, a red nucleus graphic 120, a globus pallidus graphic 122, and an optic nerve graphic 124. FIG. 3 is a grayscale image. However, the GUI can be presented in color, and the graphics representing the different anatomical structures can be presented in different colors to more clearly identify their boundaries. For example, the STN graphic 114 can be displayed in bright green, the thalamus graphic 118 can be displayed in grey, the red nucleus graphic 120 can be displayed in a muted red, the globus pallidus graphic 122 can be displayed in a muted green, and the optic nerve graphic 124 can be displayed in yellow. Where structures overlap each other, the overlapping structures can each be discernible using appropriate transparency levels.

In an example embodiment, and as shown in FIG. 3, the GUI further includes a structure menu 100 that includes a listing, e.g., by name, of one or more, e.g., all, of the separately represented structures, where each listing is displayed immediately adjacent a swatch of the color used for its representation. For example, "STN" can be displayed immediately adjacent a swatch of bright green, represented in the grayscale image of FIG. 3 as a bright box. As shown in FIG. 3, the listing can be divided into different sections that each corresponds to a respective category of information. For example, the top section of the structure menu 100 in FIG. 3 can include those displayed structures that are considered most relevant to the therapeutic stimulation being studied or applied, and the bottom section can include those displayed structures that are considered less relevant to the therapy. What is considered most relevant to the therapy can be predetermined, e.g., based on the patient's condition, such as whether the patient is a PD or Alzheimer's patient, or can be set by the clinician.

Instead of or in additional to displaying the different structures using different colors or shades, the system can use different respective hatchings for their display. The swatches of the structure menu 100 can accordingly show the respective hatchings.

Besides for anatomical structures, the processor can display in the GUI defined relevant mechanical and/or electrical structures. For example, FIG. 3 includes a lead graphic 116 representing the implanted leadwire and displayed in a bright blue, and a contact graphic 125 for each electrode contact of the leadwire, displayed in yellow. The structure menu 100 can further identify one or more of such mechanical and/or electrical structures. For example, the structure menu 100 of FIG. 3 lists "lead" adjacent a swatch of the color used for its representation.

In an example embodiment of the present invention, the system displays defined stimulation regions. For example, a user or system selected and/or defined target region, which, as described above, is an ideal area targeted for stimulation, can be displayed with a target region graphic 110. Additionally (or alternatively) a volume of estimated activation (VOA) for a given stimulation parameter set can be displayed with an active simulation graphic 112. Such areas can also be displayed with respective colors and/or hatchings. For example, the target region graphic 110 can be displayed in bright blue and the active simulation graphic 112 can be displayed in bright red. The structure menu 100 can also include a listing of one or both (or none) of these structures adjacent respective swatches of their respective colors and/or hatchings.

In an example embodiment of the present invention, the GUI is user-interactive, e.g., by point and click using an input device such as a mouse, stylus, or even the user's finger, or by keyboard manipulation, for selecting and deselecting the text listings and/or their corresponding swatches in the structure menu 100, in accordance with which the system adds or removes the respective color and/or hatching of the structure corresponding to the selected item of the structure menu 100. For example, while the STN graphic 114 is displayed in bright green, the user can select its corresponding swatch or label in the structure menu 100, in response to which selection, the system updates the GUI so that the STN graphic 114 is no longer displayed with that color. This may be helpful to allow the user to highlight those of the included structures that are of interest to the user, the other structures essentially becoming background by their grayscale, black, or other similar presentation.

In an example embodiment of the present invention, the GUI includes controls for modifying the stimulation settings of the electrode contacts, actually and/or virtually as proposed changes in a simulation to study the effects of the proposed changes to the settings on the stimulation. According to example embodiment, the system calculates scores as discussed above based on estimated overlap with one or more target and/or side effect regions.

According to an example embodiment of the present invention, the GUI includes a spill control 103 that can be manipulated by the user to slide along a spill bar 102 and/or includes an overlap control 105 that can be manipulated by the user to slide along an overlap bar 104. Where both are provided, manipulation of one may cause an automatic change of the position of the other.

The spill control 103 can be manipulated to change the amount of allowed spill of the VOA beyond the boundaries of the target region. For example, referring to FIG. 3, the spill control 103 can be shifted to the right to increase the amount of spill, and to the left to lower the amount of spill. In an alternative example embodiment, an exact amount of spill is not increased or lowered; rather, a threshold is raised or lowered. For example, according to this embodiment, the spill control 103 can be shifted to the right to raise the threshold of maximum allowed spill, and to the left to lower the threshold of maximum allowed spill.

In this regard, it is often not possible to set stimulation parameters of the electrode contacts to produce a region of activated tissue that corresponds exactly to the target region of stimulation. While increasing the amplitude of settings of one or more electrode contacts may produce a larger estimated stimulation region to fill a greater amount of the target region, such increase of amplitude often results in a larger amount of the estimated stimulation region that extends beyond the boundaries of the target stimulation region at one or more locations. Increasing the threshold amount of allowed spill therefore often allows the system to suggest stimulation parameters for filling a greater amount of the target stimulation region. In an example embodiment of the present invention, in response to the user sliding the spill control 103 to revise the spill threshold, the system accordingly modifies the spill threshold, finds a set of stimulation parameters that, if applied to the electrode contacts, is estimated to provide the greatest fill of the target region while not exceeding the spill threshold, and modifies the active simulation graphic 112. In an example embodiment, one or more electrode contacts and/or overall leadwire parameter settings can be displayed. According to this embodiment, the system can also update such settings in response to the user's sliding of the spill control 103, where such change results in a different parameter set.

The overlap control 105 can be similarly operated to increase or decrease the amount of the target region to be filled. According to an alternative example embodiment of the present invention, the overlap control 105 can be operated to raise or lower a threshold of overlap, according to which the overlap amount can be increased or decreased.

The increase of the amount of the target region to be filled may (but not necessarily) require a reduction of the spill threshold. For example, the user can slide the overlap control 105 to the right as an instruction to modify the stimulation settings so that the VOA fills a greater amount of the target region (where such parameters are feasible), but such modification of the stimulation settings may result in a VOA that spills over beyond the boundaries of the target region more than the set spill threshold. Accordingly, in such an instance, according to an example embodiment, the system automatically adjusts the spill amount/threshold in response to the user's instruction. Where this happens and the system finds parameters that would produce a VOA that more completely fills the target region as instructed by the user, and in an embodiment in which the spill control 103 is displayed besides for the overlap control 105, the system accordingly shifts the spill control 103 to the right along spill bar 102, and adjusts the active simulation graphic 112 accordingly.

Similarly, the decrease in allowed amount of spill set by user-manipulation of the spill control 103 may (but not necessarily) require a reduction in required overlap. Accordingly, in such an instance, according to an example embodiment, the system automatically adjusts the overlap amount/threshold in response to the user's instruction, and, according to an example embodiment, automatically adjusts a position of the spill control 103.

According to the embodiment in which the overlap control 105 corresponds to an overlap threshold, in an example embodiment, the overlap threshold is a minimum percentage of the target volume with which the VOA is to overlap. For example, in an example embodiment, for a minimum overlap threshold set by user-manipulation of the overlap control 105, the system determines the set of stimulation parameters that provides a VOA that meets the set minimum overlap threshold with the least spill. Similarly, in response to user-manipulation of the spill control 103, the system determines the set of stimulation parameters that provides a VOA that meets the set maximum spill threshold with the most overlap. According to an alternative example embodiment of the present invention, in response to a shift of the spill control 103 or a shift of the overlap control 105, the system determines a set of stimulation parameters that provides a best of possible VOAs (corresponding to different possible sets of stimulation parameters) that meets the thresholds, where what is considered best depends on a score calculated for the VOA, e.g., according to one of the scoring methods described above (which can include consideration of side effect regions as well).

According to an alternative example embodiment, the overlap threshold is a maximum percentage of the target volume with which the VOA is to overlap. In response to user-manipulation of the overlap control 105, the system determines the set of stimulation parameters that provides a VOA with the most overlap not exceeding the maximum threshold. Alternatively, the system determines the set of stimulation parameters that provides a VOA having the best score of VOAs meeting the maximum threshold, for example, where the score is determined using one of the methods described above (which can include consideration of side effect regions as well).

According to an alternative example embodiment, whether the set threshold is a minimum or a maximum depends on a direction in which the user moves the overlap control 105. For example, if the user shifts the overlap control 105 to increase the threshold, then it is treated as a minimum threshold, and if the user shifts the overlap control 105 to decrease the threshold, then it is treated as a maximum threshold.

According to an example embodiment, where the user slides the overlap control 105 to increase the fill amount by more than is feasible, the system finds the parameters that produces the greatest fill amount, and automatically adjusts the position of the overlap control 105 accordingly. Similarly, where the user slides the spill control 103 to increase the spill threshold by an amount not required to obtain the greatest feasible fill amount of the target region, according to an example embodiment, the system adjusts the spill threshold to the spill amount required for the greatest fill amount of the target region.

In an example embodiment of the present invention, the system textually quantifies the spill amount and/or overlap amount. For example, FIG. 3 shows that the spill amount is 18% (and that the amount by which the VOA does not spill beyond the target region is 82%), and that the overlap amount is 48% (and that the amount by which the VOA does not overlap is 52%). The spill amount can be expressed as a percentage of the VOA, and the overlap amount can be expressed as a percentage of the target region. For example, with reference to FIG. 3, 82% of the VOA is within the target region and 18% of the VOA spills beyond the boundaries of the target region; and 48% of the target region is filled by the VOA and 52% of the target region is not filled by the VOA. According to an alternative example embodiment, the spill corresponds to $$\frac{V \cap T^c}{T^c}$$

and is therefore dependent on a predefined considered area in which the VOA and target regions can be positioned.

Alternatively, other measures can be used. For example, the system can express the amounts as any number between 0 and 1. With respect to spill amount, the system can, for example, determine the greatest technically and/or safely feasible VOA and set the spill amount of 1 as representing the spill resulting by such settings. Similarly, with respect to overlap amount, the system can, for example, determine the greatest amount of the target region that can technically and/or safely possibly be filled, and set the overlap amount of 1 as representing such a fill amount.

Figure 4:
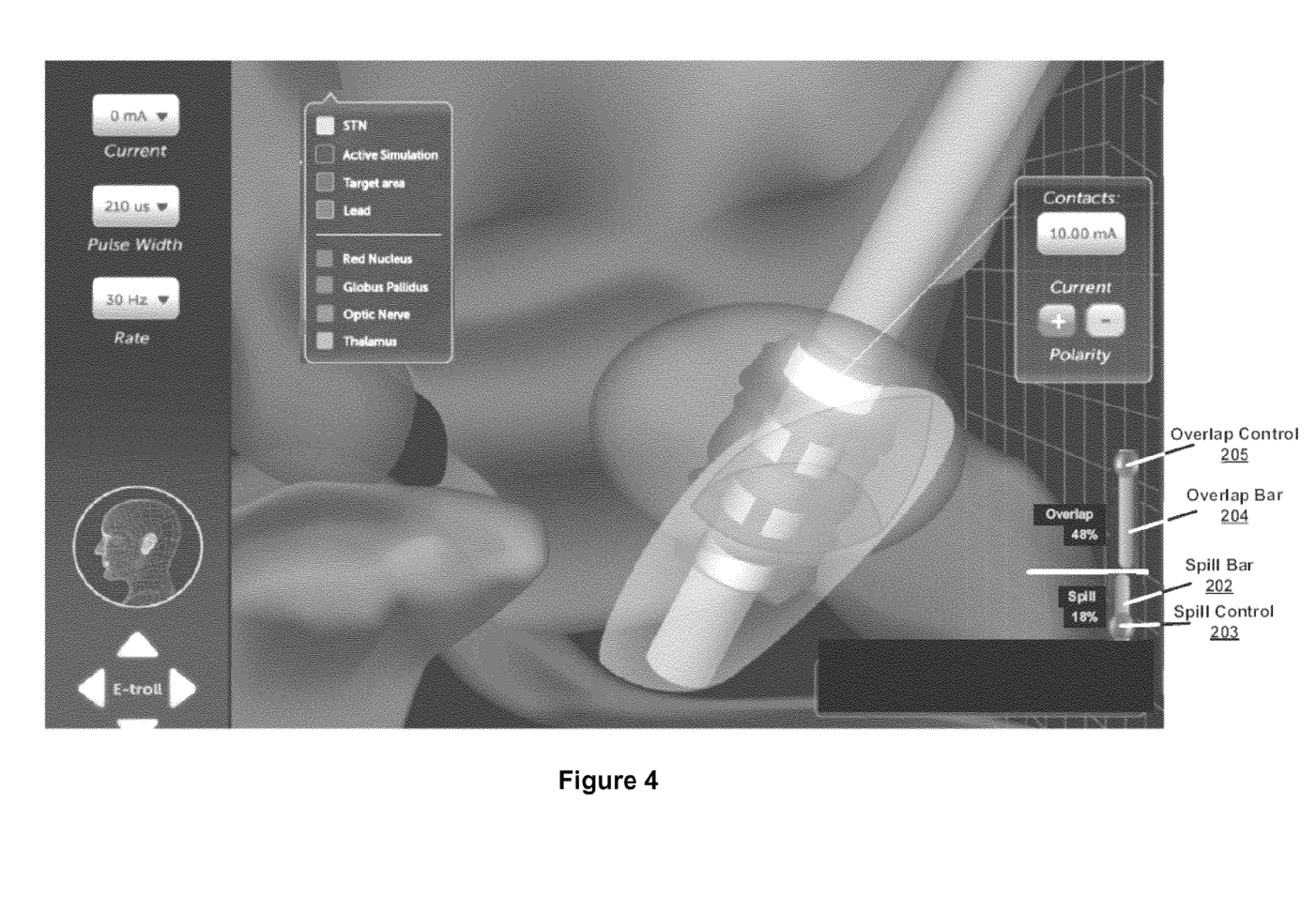
FIG. 4 is a screenshot of a variation of the graphical user interface of FIG. 3, with modified spill and overlap controls, according to an example embodiment of the present invention.

FIG. 4 shows an alternative example embodiment of the spill and overlap bars and controls. In FIG. 4, an overlap control 205 is displayed as a terminal of an overlap bar 204, and can be dragged upwards or downwards to correspondingly lengthen or shorten the overlap bar 204 and correspondingly raise or lower the overlap amount. Similarly, a spill control 203 is displayed as a terminal of a spill bar 202, and can be dragged downwards or upwards to correspondingly lengthen or shorten the spill bar 202 and correspondingly raise or lower the spill amount. Other graphical representations can be used instead. For example, the controls 203 and 205 can be omitted, and the bars themselves can be dragged in one of the directions to change their respective lengths. Alternatively, arrows can be displayed and selectable for changing the lengths of the bars. Alternatively, the lengths can be modifiable by manipulation of keys of a keyboard without manipulation of a graphical control.

Figure 6:
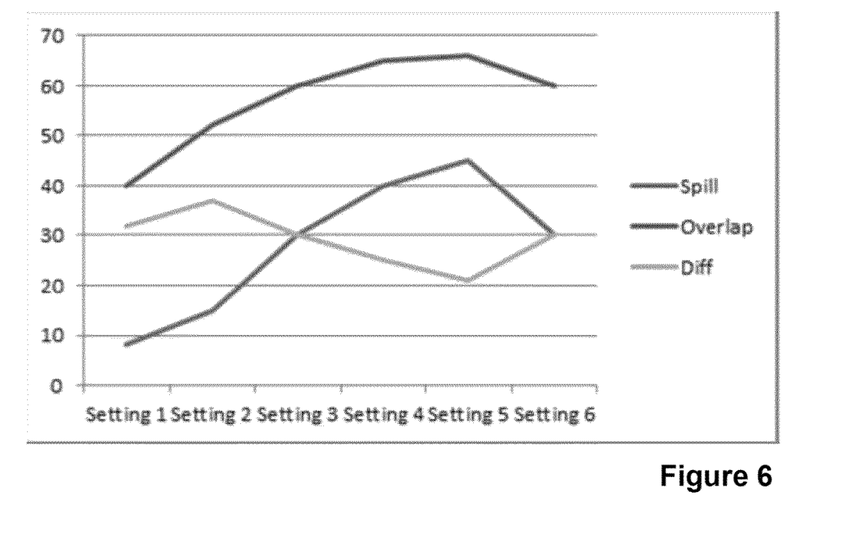
FIG. 6 is a graph showing a relationship between volume overlap and spill at various stimulation settings.

In an example embodiment of the present invention, the system records the spill and overlap amounts of each of a plurality of stimulations parameter sets actually applied or simulated over time, and generates and outputs to the user a graph, as illustrated in FIG. 6, showing the different spill levels, overlap levels, and/or differences therebetween. The user can use such information, for example, in deciding the level of overlap to try to attain. In the graph of FIG. 6, the line beginning at approximately 40 represents the overlap amount, the line beginning just below 10 represents the spill amount, and the line beginning just above 30 represents the difference between the overlap and spill amounts. For example, the spill curve can plot percentages of respective VOAs (corresponding to the settings corresponding to one of the axes of the graph) that spill beyond the target volume, the overlap curve can plot percentages of the target volume that are overlapped by the respective VOAs, and the difference curve can plot the differences between those values. Alternatively, the spill curve can plot the values of $$\frac{V \cap T^c}{T^c}$$

calculated for the different settings and the overlap curve can plot the values of $$\frac{V \cap T}{T}$$

calculated for the different settings. The latter embodiment may be advantageous because the same area is considered for evaluating the spill values for the different VOAs, whereas according to the former embodiment, the percentages are of the complete volume of each of the VOAs themselves, and are consequently percentages of different sized volumes. According to yet another embodiment, the spill values of the spill curve are numbers of voxels of the respective VOAs that do not overlap the target volume, and the overlap values of the overlap curve are numbers of voxels of the respective VOAs that overlap the target volume. Whichever calculations are used for obtaining the spill and overlap values, the difference curve plots the differences between those calculated values for a plurality of sets of stimulation parameters.

Alternatively, scores can be calculated and output, e.g., in graphs, as described above, e.g., using eq. 1, eq. 2, the ROC graph(s), the mutual information formula, or the entropy formula.

Referring again to FIG. 3, in an example embodiment of the present invention, the system is configured to display a contact control box 106 within, e.g., overlaid on, the anatomical atlas/image for modifying the parameters of a respective electrode contact. For example, a separate respective contact control box 106 can simultaneously be displayed for each of the electrode contacts. Alternatively, each of the contact graphics 125 can be separately selectable, in response to which selection the respective contact control box 106 corresponding to the selected contact graphic 125 is selectively displayed, the others not being displayed. Alternatively, when none of the electrode contact graphics 125 are selected, the system omits from the display all of the contact control boxes 106, and when any one of the contact graphics 125 is selected, the system responsively displays all of the contact control boxes 106, since the settings of one contact may affect the user's decision as to how to set another of the contacts. According to this embodiment, after the contact is selected, the user can deselect, e.g., by selecting any part of the GUI other than any of the contacts graphics 125 and contact control boxes 106, or by reselecting the same contact graphic 125.

In an example embodiment, the user can interact with displayed components of the displayed contact control box 106 to modify the settings of the electrode contact to which it corresponds. Such interaction can be, for example, by way of mouse, stylus, finger, or keyboard entry.

In an example embodiment of the present invention, the control elements displayed within the contact control box 106 are limited to only those with which interaction provides for modification of respective settings of the particular electrode to which it corresponds. Control elements for modifying settings of the leadwire as a whole and that are not specific to any one electrode can be displayed in a separate region of the GUI. For example, FIG. 3 shows display of such controls at the left side of the GUI separate from the anatomical image and/or atlas display.

In an example embodiment of the present invention, responsive to selection of one of the contact graphics 125, the system modifies the display of the selected contact graphic 125. For example, it can be displayed with a different color or in a different, e.g., brighter, shade of the same color, to visually indicate to the user which contact has been selected and/or for which the contact control box 106 is displayed.

Figure 7:
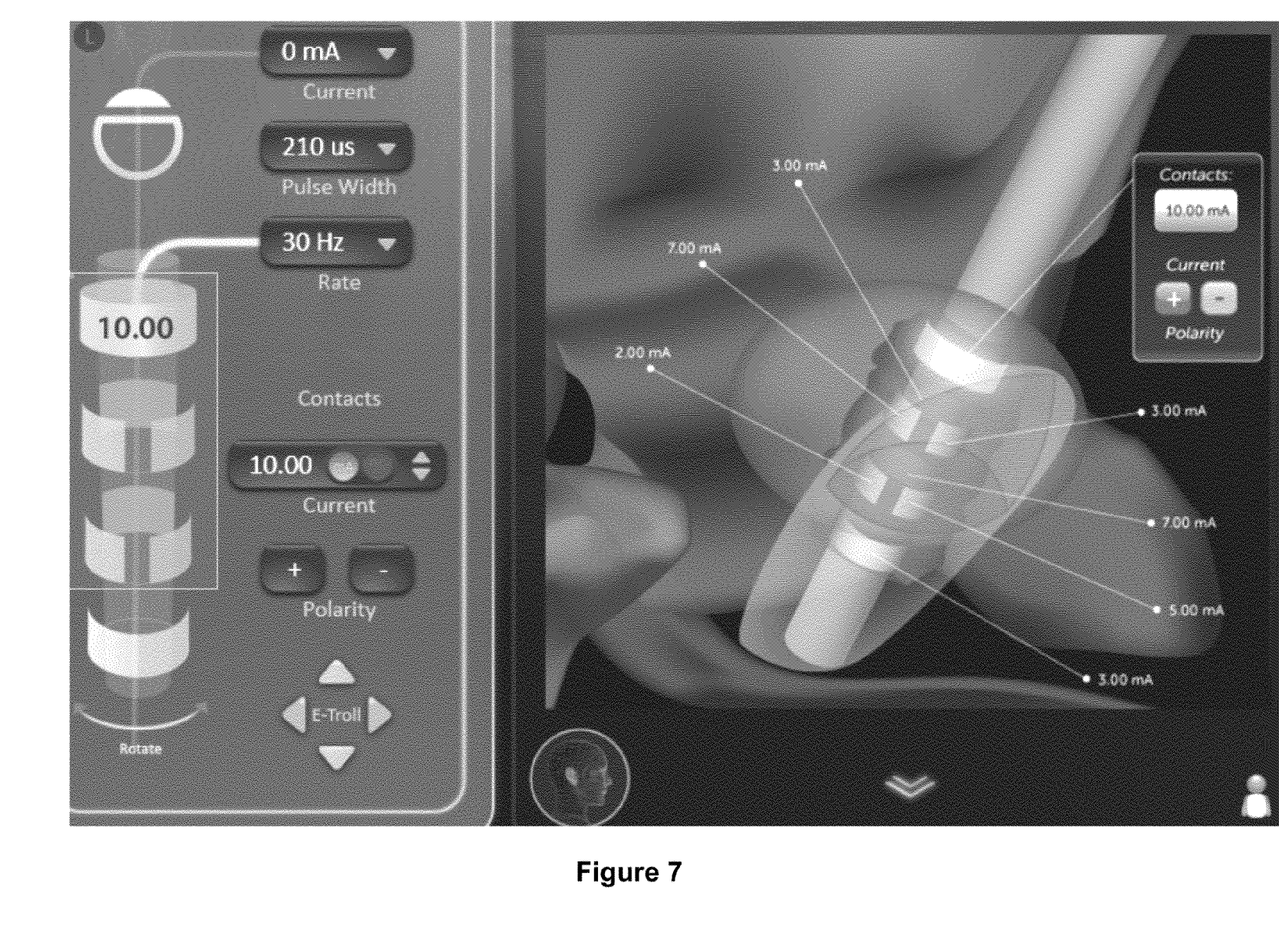
FIG. 7 is a screenshot of a graphical user interface, in which a contact control box is displayed for a selected contact, and stimulation parameters are displayed for non-selected contacts, according to an example embodiment of the present invention.

In an example embodiment of the present invention, even where only a single contact control box 106 corresponding to a selected one of the contact graphics 125 is displayed, one or more presently set settings of the other contacts are displayed in the anatomical image and/or atlas alongside the respective other contacts and/or with a connector from the displayed settings to the respective contacts to which they correspond, e.g., as shown in FIG. 7.

Figure 5:
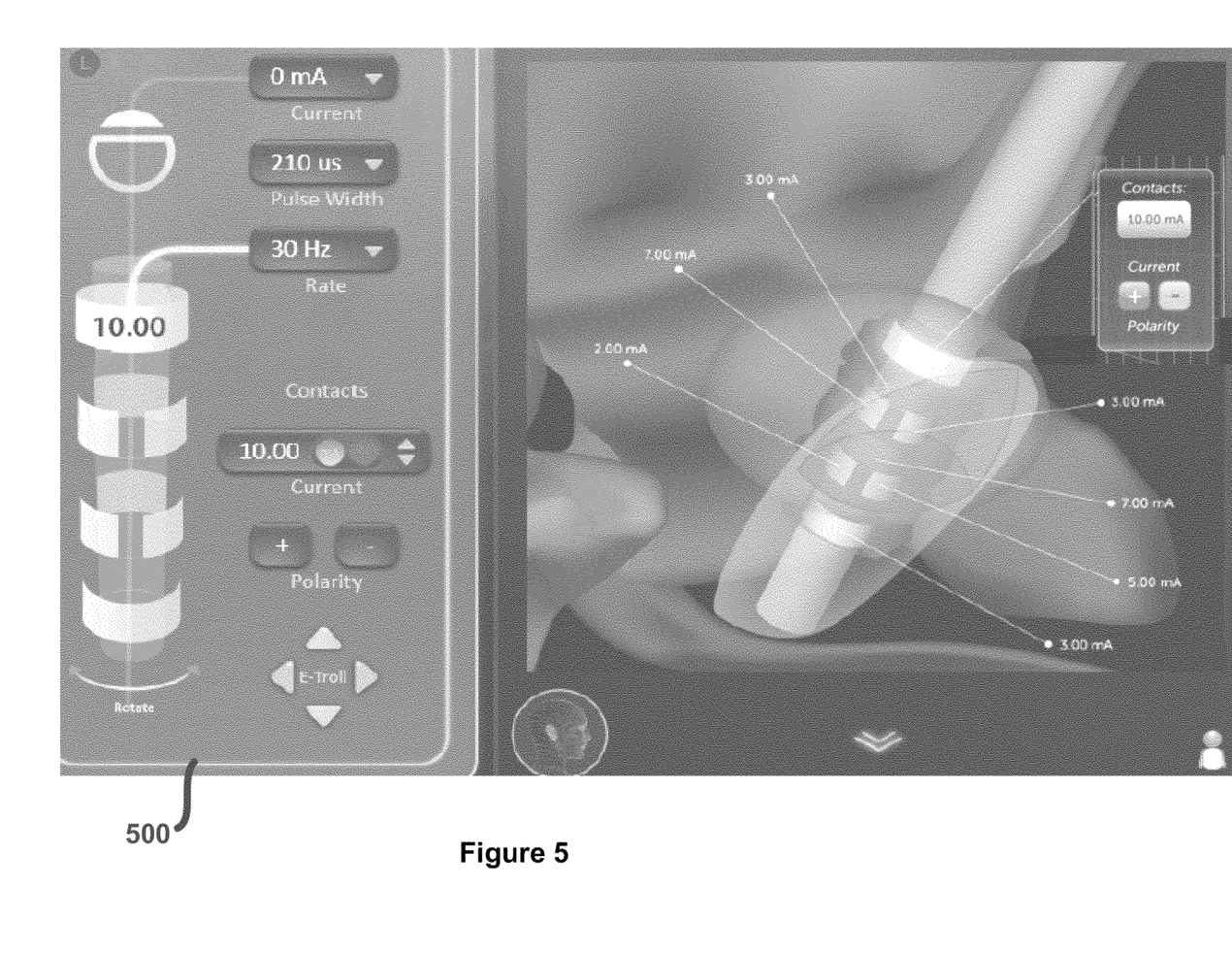
FIG. 5 is a screenshot of a graphical user interface for displaying a leadwire control box and corresponding highlighting of selected electrodes, according to an example embodiment of the present invention.

In an example embodiment of the present invention, the system displays a leadwire control box 500 in the GUI, e.g., beside the anatomical image and/or atlas, e.g., as shown in FIG. 5. The leadwire control box 500 can include controls for modifying various settings of the leadwire and its electrode contacts. The leadwire control box can include a model of the leadwire, including respective electrode components representing each of the electrode contacts of the leadwire. Each of the displayed electrode components can be separately selectable, in response to which selection the selected electrode component is highlighted and its settings can be modifiable by interaction with other displayed controls. In an example embodiment, besides for or instead of highlighting the selected electrode component of the model leadwire of the separate leadwire control box 500, the respective contact graphic 125 displayed in the anatomical image and/or atlas is highlighted in response to the selection of the electrode component in the leadwire control box 500, thereby visually informing the user of the relationship of the selected electrode to the displayed anatomical image and/or atlas. In an example embodiment, the respective contact control box 106 corresponding to the selected electrode contact can be displayed in addition to or instead of the control elements of the leadwire control box 500 for controlling the specific electrode that has been selected.

The various methods described herein can be practiced, each alone, or in various combinations.

An example embodiment of the present invention is directed to a processor, which may be implemented using any conventional processing circuit and device or combination thereof, e.g., a Central Processing Unit (CPU) of a Personal Computer (PC) or other workstation processor, to execute code provided, e.g., on a hardware computer-readable medium including any conventional memory device, to perform any of the methods described herein, alone or in combination. In certain example embodiments, the processor may be embodied in a remote control device. The memory device may include any conventional permanent and/or temporary memory circuits or combination thereof, a non-exhaustive list of which includes Random Access Memory (RAM), Read Only Memory (ROM), Compact Disks (CD), Digital Versatile Disk (DVD), and magnetic tape.

An example embodiment of the present invention is directed to a hardware computer-readable medium, e.g., as described above, having stored thereon instructions executable by a processor to perform the methods described herein.

An example embodiment of the present invention is directed to a method, e.g., of a hardware component or machine, of transmitting instructions executable by a processor to perform the methods described herein.

An example embodiment of the present invention is directed to an output device configured to output any of the GUIs described herein.

The above description is intended to be illustrative, and not restrictive. Those skilled in the art can appreciate from the foregoing description that the present invention can be implemented in a variety of forms, and that the various embodiments can be implemented alone or in combination. Therefore, while the embodiments of the present invention have been described in connection with particular examples thereof, the true scope of the embodiments and/or methods of the present invention should not be so limited since other modifications will become apparent to the skilled practitioner upon a study of the drawings, specification, and the following claims.

What is claimed is:

1. A computer-implemented method, comprising:
generating, by a computer processor, a graphical user interface including a model of anatomical structures of a patient, overlaid with components that are modifiable in response to changes in stimulation parameter settings of a leadwire implanted in an anatomical region of the patient in which the anatomical structures are located;
for each of at least a subset of the modeled anatomical structures, overlaying, by the processor, a respective graphical indicium over the respective modeled anatomical structure that distinguishes the respective modeled anatomical structure from other modeled structures in the graphical user interface;
in accordance with an identified therapy, sorting, by the processor, the modeled anatomical structures by degree of relevance of the respective modeled anatomical structures to the identified therapy; and
displaying, by the processor, a legend that includes swatches of different ones of the graphical indicia adjacent respective textual descriptions of the modeled anatomical structures to which the graphical indicia correspond, wherein the legend includes a first section in which a first set of the graphical indicia and their corresponding textual descriptions are displayed and a second section in which a second set of the graphical indicia and their corresponding textual descriptions are displayed, the graphical indicia and corresponding textual descriptions being grouped into the first and second sets according to the sorting of the modeled anatomical structures.

2. The method of claim 1, further comprising:
receiving user-input of a medical indication, wherein the sets of the graphical indicia and the corresponding textual descriptions are based on the user-input medical indication.

3. The method of claim 1, further comprising:
displaying a marker separating the first and second sets.

4. The method of claim 1, wherein colors are used as the graphical indicia.

5. The method of claim 1, wherein hatching patterns are used as the graphical indicia.

6. The method of claim 1, wherein, in a section of the graphical user interface in which modeled anatomical structures, for which respective ones of the graphical indicia are displayed, overlap, at least one of the graphical indicia is provided with a transparency such that the graphical indicia of all of the overlapping modeled anatomical structures are displayed.

7. The method of claim 1, wherein the graphical user interface includes a graphical model of the leadwire overlaid with a respective graphical indicium represented in the legend.

8. The method of claim 1, wherein the graphical user interface includes a graphical model of at least one of an implanted mechanical component and an implanted electrical component with respective graphical indicia represented in the legend.

9. The method of claim 1, wherein the modeled anatomical structures are obtained from image data of the patient.

10. The method of claim 1, wherein the graphical user interface includes a graphical representation of an anatomical region targeted for stimulation by the leadwire with a respective graphical indicium represented in the legend.

11. The method of claim 1, wherein the graphical user interface includes a graphical representation of an anatomical region estimated to be activated by the leadwire according to received stimulation settings with a respective graphical indicium represented in the legend.

12. The method of claim 1, wherein respective ones of the swatches are user-selectable to toggle between display and removal from display of the corresponding graphical indicia, such that, while all of the modeled anatomical structures remain displayed, different sets of the modeled anatomical structures are able to be accentuated by toggling between which ones of the displayed modeled anatomical structures are overlaid with respective graphical indicia.

13. A computer system, comprising:
a display device; and
a processor configured to:
generate a graphical user interface in the display device including a model of anatomical structures of a patient, overlaid with components that are modifiable in response to changes in stimulation parameter settings of a leadwire implanted in an anatomical region of the patient in which the anatomical structures are located;
for each of at least a subset of the modeled anatomical structures, overlay a respective graphical indicium over the respective modeled anatomical structure that distinguishes the respective modeled anatomical structure from other modeled structures in the graphical user interface;
in accordance with an identified therapy, sort the modeled anatomical structure by degree of relevance of the respective modeled anatomical structures to the identified therapy; and
display in the display device a legend that includes swatches of different ones of the graphical indicia adjacent respective textual descriptions of the modeled anatomical structures to which the graphical indicia correspond, wherein the legend includes a first section in which a first set of the graphical indicia and their corresponding textual descriptions are displayed and a second section in which a second set of the graphical indicia and their corresponding textual descriptions are displayed, the graphical indicia and corresponding textual descriptions being grouped into the first and second sets according to the sorting of the modeled anatomical structures.

14. A non-transitory computer-readable medium on which are stored instructions executable by a processor, the instructions which, when executed by the processor, cause the processor to perform a method, the method comprising:
generating a graphical user interface including a model of anatomical structures of a patient, overlaid with components that are modifiable in response to changes in stimulation parameter settings of a leadwire implanted in an anatomical region of the patient in which the anatomical structures are located;
for each of at least a subset of the modeled anatomical structures, overlaying a respective graphical indicium over the respective modeled anatomical structure that distinguishes the respective modeled anatomical structure from other modeled structures in the graphical user interface;
in accordance with an identified therapy, sorting the modeled anatomical structure by degree of relevance of the respective modeled anatomical structures to the identified therapy; and
displaying a legend that includes swatches of different ones of the graphical indicia adjacent respective textual descriptions of the modeled anatomical structures to which the graphical indicia correspond, wherein the legend includes a first section in which a first set of the graphical indicia and their corresponding textual descriptions are displayed and a second section in which a second set of the graphical indicia and their corresponding textual descriptions are displayed, the graphical indicia and corresponding textual descriptions being grouped into the first and second sets according to the sorting of the modeled anatomical structures.

15. A computer-implemented method comprising:
displaying, by a computer processor, a first model of a leadwire implanted in a patient and including electrodes controllable for stimulating an anatomical region of the patient about the leadwire, wherein the leadwire model includes representations of the electrodes;
responsive to selection of one of the electrode representations, displaying by the processor a user-interactional control, in response to user-interaction with which the processor is configured to modify an electrical parameter of the electrode whose representation has been selected, wherein, responsive to the selection of the one of the electrode representation, the processor displays a respective user-interactional control for each of the electrode representations;
displaying, in a first display region and by the processor, graphical representations of anatomical structures in a region of the patient in which the leadwire is implanted, the first model of the leadwire and a portion of the graphical representations being overlaid, wherein the user-interactional control is overlaid on a portion of the graphical representations;
displaying, in a second display region and by the processor, a second model of the leadwire in a display region separate from a display region in which the graphical representations of the anatomical structure are displayed, wherein the one of the electrode representations is selectable in both of the first and second electrode leadwire models; and
responsive to the selection of the one of the electrode representations by clicking the one of the electrode representations in one of the first and second display regions, highlighting, by the processor, the selected electrode representation in the leadwire models of both the first and second display regions.

16. The method of claim 15, further comprising:
responsive to a deselection of the one of the electrode representations, removing the user-interactional control from display.

17. The method of claim 15, wherein the user-interactional control includes at least one button for modifying at least one of (a) an electrical amplitude value of the respective electrode and (b) a polarity of the respective electrode, the method further comprising:

displaying user-interactional leadwire controls for modifying electrical parameters of the leadwire that are not electrode-specific, the user-interactional leadwire controls being statically displayed regardless of any electrode representation selections, and the user-interactional leadwire controls including at least one button for modifying at least one of (a) a pulse width and (b) a rate for stimulation by the leadwire as a whole.

18. A non-transitory computer-readable medium on which are stored instructions executable by a processor, the instructions which, when executed by the processor, cause the processor to perform a method, the method comprising:

displaying a first model of a leadwire implanted in a patient and including electrodes controllable for stimulating an anatomical region of the patient about the leadwire, wherein the leadwire model includes representations of the electrodes;

responsive to selection of one of the electrode representations, displaying a user-interactional control, in response to user-interaction with which the processor is configured to modify an electrical parameter of the electrode whose representation has been selected, wherein, responsive to the selection of the one of the electrode representation, the processor displays a respective user-interactional control for each of the electrode representations;

displaying in a first display region graphical representations of anatomical structures in a region of the patient in which the leadwire is implanted, the first model of the leadwire and a portion of the graphical representations being overlaid, wherein the user-interactional control is overlaid on a portion of the graphical representations;

displaying in a second display region a second model of the leadwire in a display region separate from a display region in which the graphical representations of the anatomical structure are displayed, wherein the one of the electrode representations is selectable in both of the first and second electrode leadwire models; and responsive to the selection of the one of the electrode representations by clicking the one of the electrode representations in one of the first and second display regions, highlighting the selected electrode representation in the leadwire models of both the first and second display regions.

19. A computer system comprising:
a display device; and
a processor configured to:

display in the display device a first model of a leadwire implanted in a patient and including electrodes controllable for stimulating an anatomical region of the patient about the leadwire, wherein the leadwire model includes representations of the electrodes;

responsive to selection of one of the electrode representations, display in the display device a user-interactional control, in response to user-interaction with which the processor is configured to modify an electrical parameter of the electrode whose representation has been selected, wherein, responsive to the selection of the one of the electrode representation, the processor displays a respective user-interactional control for each of the electrode representations;

display in a first display region graphical representations of anatomical structures in a region of the patient in which the leadwire is implanted, the first model of the leadwire and a portion of the graphical representations being overlaid, wherein the user-interactional control is overlaid on a portion of the graphical representations;

display in a second display region a second model of the leadwire in a display region separate from a display region in which the graphical representations of the anatomical structure are displayed, wherein the one of the electrode representations is selectable in both of the first and second electrode leadwire models; and responsive to the selection of the one of the electrode representations by clicking the one of the electrode representations in one of the first and second display regions, highlight the selected electrode representation in the leadwire models of both the first and second display regions.

* * * * *